United States Patent
Wu et al.

(10) Patent No.: US 12,168,746 B2
(45) Date of Patent: Dec. 17, 2024

(54) THERMALLY ACTIVATED DELAYED FLUORESCENT MATERIAL, PREPARING METHOD THEREOF, AND ORGANIC ELECTROLUMINESCENT DEVICE

(71) Applicant: Wuhan China Star Optoelectronics Semiconductor Display Technology Co., Ltd., Wuhan (CN)

(72) Inventors: Kailong Wu, Wuhan (CN); Qu Zhang, Wuhan (CN)

(73) Assignee: Wuhan China Star Optoelectronics Semiconductor Display Technology Co., Ltd., Hubei (CN)

( * ) Notice: Subject to any disclaimer, the term of this patent is extended or adjusted under 35 U.S.C. 154(b) by 1212 days.

(21) Appl. No.: 16/957,488

(22) PCT Filed: Apr. 10, 2020

(86) PCT No.: PCT/CN2020/084212
§ 371 (c)(1),
(2) Date: Jun. 24, 2020

(87) PCT Pub. No.: WO2021/189553
PCT Pub. Date: Sep. 30, 2021

(65) Prior Publication Data
US 2023/0137446 A1 May 4, 2023

(30) Foreign Application Priority Data
Mar. 26, 2020 (CN) .......................... 202010223465.9

(51) Int. Cl.
| | | |
|---|---|---|
| C09K 11/06 | (2006.01) | |
| C07D 219/02 | (2006.01) | |
| C07D 401/10 | (2006.01) | |
| C07D 401/14 | (2006.01) | |
| H10K 50/11 | (2023.01) | |
| H10K 85/60 | (2023.01) | |
| H10K 101/20 | (2023.01) | |

(52) U.S. Cl.
CPC ............ *C09K 11/06* (2013.01); *C07D 219/02* (2013.01); *C07D 401/10* (2013.01); *C07D 401/14* (2013.01); *H10K 50/11* (2023.02); *H10K 85/6572* (2023.02); *C09K 2211/1011* (2013.01); *C09K 2211/1096* (2013.01); *H10K 2101/20* (2023.02)

(58) Field of Classification Search
CPC ............. H10K 85/6572; H10K 85/657; H10K 85/615; H10K 50/11; H10K 2101/20; C09K 11/06; C09K 2211/1011; C09K 2211/1096; C07D 219/02; C07D 401/10; C07D 401/14

See application file for complete search history.

(56) References Cited

U.S. PATENT DOCUMENTS

| | | | |
|---|---|---|---|
| 2003/0044680 A1 | 3/2003 | Umemoto | |
| 2003/0081432 A1 | 5/2003 | Umemoto | |
| 2013/0306945 A1* | 11/2013 | Seo .................. | H10K 50/16 257/40 |

FOREIGN PATENT DOCUMENTS

CN 109943320 6/2019

OTHER PUBLICATIONS

Trost et al. "Perturbed [12] Annulenes. Derivatives of Dibenzo[cd,gh]Pentalene", Journal of the American Chemical Society, 97(9): 2438-2451, Apr. 30, 1975.

* cited by examiner

*Primary Examiner* — Dylan C Kershner
(74) *Attorney, Agent, or Firm* — PV IP PC; Wei Te Chung

(57) ABSTRACT

A thermally activated delayed fluorescent material, preparing method thereof, and an organic electroluminescent device are disclosed. The organic electroluminescent device includes an anode layer, a cathode layer, and a light-emitting layer disposed between the anode layer and the cathode layer. The light-emitting layer includes a thermally activated delayed fluorescent material. A structural formula of the thermally activated delayed fluorescent material is shown in the following structural formula I:

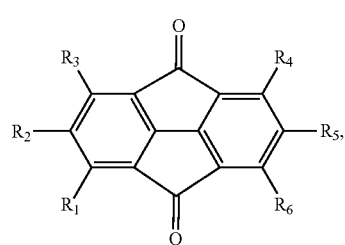

and $R_1$-$R_6$ are electron donor units.

8 Claims, 2 Drawing Sheets

THERMALLY ACTIVATED DELAYED FLUORESCENT MATERIAL, PREPARING METHOD THEREOF, AND ORGANIC ELECTROLUMINESCENT DEVICE

RELATED APPLICATIONS

This application is a National Phase of PCT Patent Application No. PCT/CN2020/084212 having International filing date of Apr. 10, 2020, which claims the benefit of priority of Chinese Patent Application No. 202010223465.9, filed on Mar. 26, 2020. The contents of the above applications are all incorporated by reference as if fully set forth herein in their entirety.

FIELD AND BACKGROUND OF THE INVENTION

The present application relates to the field of display technologies, and more particularly, to a thermally activated delayed fluorescent material, preparing method thereof, and an organic electroluminescent device.

Photoelectric conversion efficiency is an important parameter for evaluating organic light-emitting diodes (OLEDs). Since the advent of OLEDs, various luminescent material based on fluorescence and phosphorescence have been developed to improve the luminous efficiency of the OLEDs. The OLEDs based on the fluorescent material have the characteristics of high stability. However, due to the limitations of the quantum statistics laws, under the action of the electrical activation, the ratio of the singlet exciton to the triplet exciton is 1:3, so that the internal electroluminescence quantum efficiency of the traditional fluorescent material is limited to 25%. Phosphorescent material can utilize triplet excitons due to the use of the spin-orbit coupling principle of heavy atoms, and the internal electron luminescence quantum efficiency is 100% according to the theory.

However, the OLEDs based on the phosphorescent material have a significant efficiency roll-off effect. That is, the luminous efficiency decreases rapidly with the increase of current or voltage, which is particularly disadvantageous for the application of the OLEDs with high brightness. In addition, it is needed to use precious metals, which are expensive, in the phosphorescent material. Thus, it is not conducive to reduce the manufacturing costs of the display devices.

In order to overcome these shortcomings of the luminescent material, professor Adachi and others of Kyushu University in Japan proposed the reverse intersystem crossing effect to fully utilize the thermally activated delayed fluorescence (TADF) effect of triplet excitons. In this way, organic compounds without heavy metal atoms can be used to achieve high efficiency comparable to phosphorescent OLEDs. Refer to C. Adachi, et. al., Nature, Vol 492, 234, (2012). Although TADF materials have been developed for several years, the knowledge about the TADF materials have been accumulated, and high-efficient and stable red, green and blue TADF materials have also been reported, there are few types, and choices of the materials are still insufficient. In the case where most materials are used in OLED devices, the concentration of triplet excitons increases under high voltage and current, and the reverse intersystem crossing rate is limited, which leads to serious quenching of excitons, large energy loss of excitons, and a significant decrease and quickly decay in device efficiency. Thus, the stability of the devices needs to be improved.

SUMMARY OF THE INVENTION

Technical Problems

The embodiments of the present application provide a thermally activated delayed fluorescent material, a preparing method thereof, and an organic electroluminescent device, to solve a technical problem that the current thermally activated delayed fluorescent material used in OLED devices has a fast decay rate, resulting in a significant decrease in the efficiency of the OLED devices, thereby affecting the stability of the OLED devices.

Technical Solutions

In order to solve the above problems, the technical solutions provided by the present application are as follows:

An embodiment of the present application provides a thermally activated delayed fluorescent material, having a structural formula shown in the following formula I:

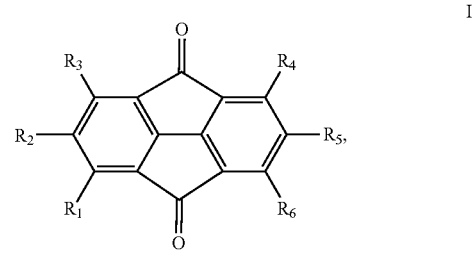

wherein $R_1$-$R_6$ are electron donor units.

In at least one embodiment of the present application, $R_1$-$R_6$ are independently selected from one of the following structural formulas:

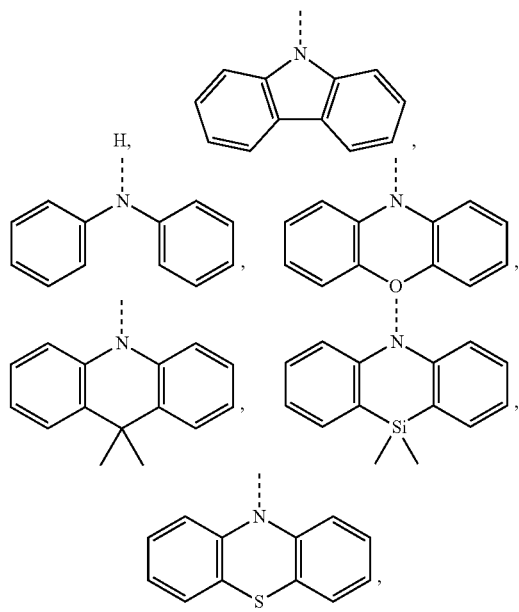

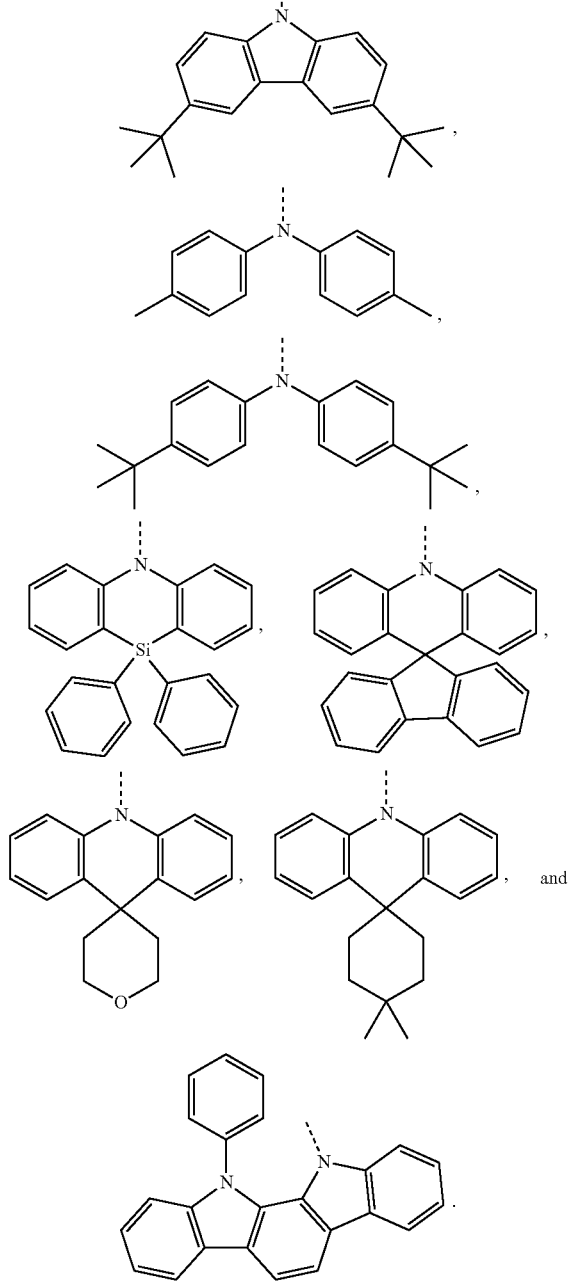

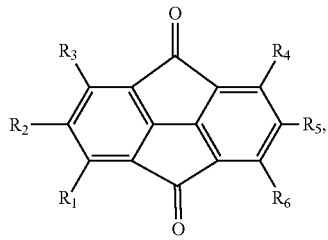

wherein $R_1$-$R_6$ are electron donor units.

In at least one embodiment of the present application, $R_1$-$R_6$ are independently selected from one of the following structural formulas:

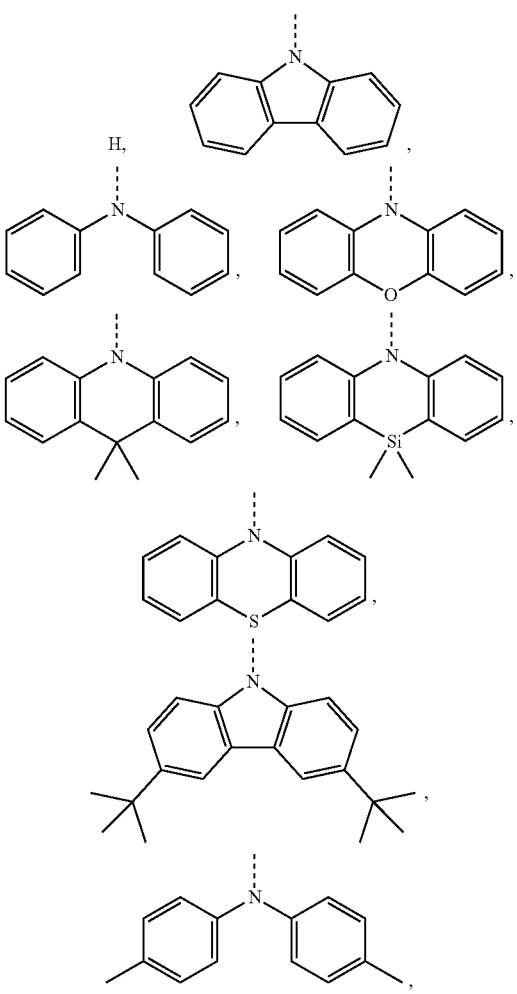

An embodiment of the present application further provides a method of preparing a thermally activated delayed fluorescent material, comprising the following steps:

a step S10 of adding a catalyst, an alkaline substance, and a solvent into a first reactant and a second reactant, wherein the first reactant is a bromide of cyclopenta [def]fluorene-4,8-dione;

a step S20 of obtaining a reaction solution through a substitution reaction occurring between the first reactant and the second reactant; and a step S30 of removing an impurity from the reaction solution to obtain the thermally activated delayed fluorescent material having a structural formula of:

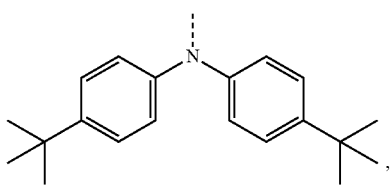

-continued

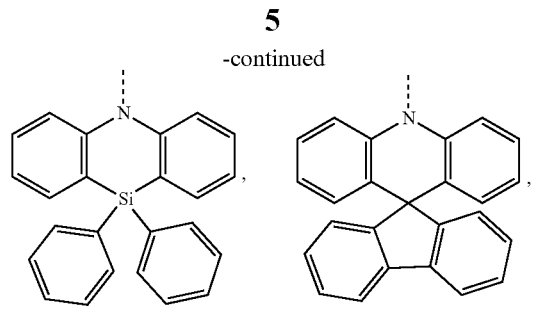

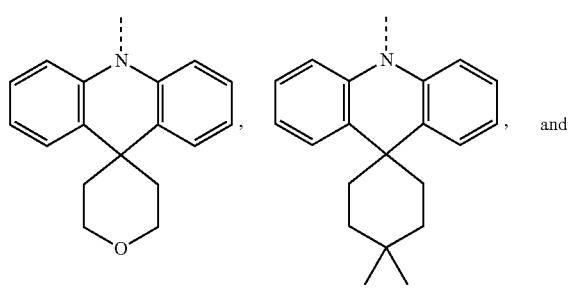

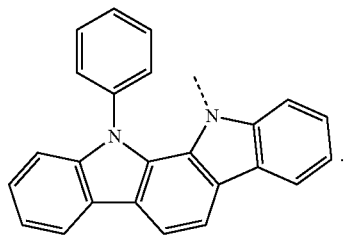

In at least one embodiment of the present application, the second reactant is one or any combination of a hydride of $R_1$, a hydride of $R_2$, a hydride of $R_3$, a hydride of $R_4$, a hydride of $R_5$, and a hydride of $R_6$.

In at least one embodiment of the present application, the first reactant is selected from one of the following structural formulas:

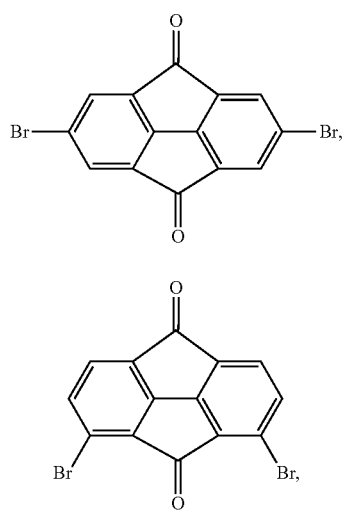

-continued

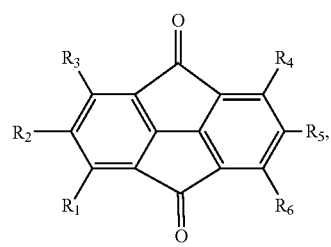

In at least one embodiment of the present application, the catalyst includes tris (dibenzylideneacetone), the alkaline substance is sodium tert-butoxide, and the solvent is anhydrous toluene.

In at least one embodiment of the present application, a reaction temperature of the substitution reaction is 80 degrees Celsius, and a reaction time of the substitution reaction is 24 hours.

In at least one embodiment of the present application, the step S30 includes:

pouring the reaction solution into saturated saline, and conducting suction filtration to obtain a red solid; and isolating and purifying the red solid by column chromatography to obtain the thermally activated delayed fluorescent material.

An embodiment of the present application further provides an organic electroluminescent device, comprising: an anode layer, a cathode layer, and a light-emitting layer disposed between the anode layer and the cathode layer, wherein the light-emitting layer includes a thermally activated delayed fluorescent material.

In at least one embodiment of the present application, a structural formula of the thermally activated delayed fluorescent material is shown in the following structural formula I:

I wherein $R_1$-$R_6$ are electron donor units.

In at least one embodiment of the present application, $R_1$-$R_6$ are independently selected from one of the following structural formulas:

In at least one embodiment of the present application, a method of preparing the thermally activated delayed fluorescent material comprises the following steps:
- a step S10 of adding a catalyst, an alkaline substance, and a solvent into a first reactant and a second reactant, wherein the first reactant is a bromide of cyclopenta[def]fluorene-4,8-dione;
- a step S20 of obtaining a reaction solution through a substitution reaction occurring between the first reactant and the second reactant; and
- a step S30 of removing an impurity from the reaction solution to obtain the thermally activated delayed fluorescent material having the structural formula of:

wherein $R_1$-$R_6$ are electron donor units.

In at least one embodiment of the present application, the second reactant is one or any combination of a hydride of $R_1$, a hydride of $R_2$, a hydride of $R_3$, a hydride of $R_4$, a hydride of $R_5$, and a hydride of $R_6$.

In at least one embodiment of the present application, the first reactant is selected from one of the following structural formulas:

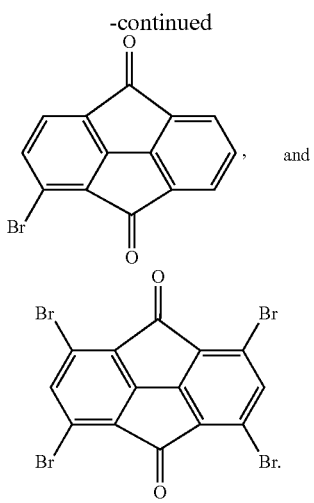

, and

In at least one embodiment of the present application, the catalyst comprises tris (dibenzylideneacetone), the alkaline substance is sodium tert-butoxide, and the solvent is anhydrous toluene.

In at least one embodiment of the present application, a reaction temperature of the substitution reaction is 80 degrees Celsius, and a reaction time of the substitution reaction is 24 hours.

In at least one embodiment of the present application, the step S30 includes:

pouring the reaction solution into saturated saline, and conducting suction filtration to obtain a red solid; and isolating and purifying the red solid by column chromatography to obtain the thermally activated delayed fluorescent material.

Beneficial Effect

By using the cyclopenta[def]fluorene-4,8-dione as the acceptor units, the conjugated effect of the molecular acceptor units is increased, the electron withdrawing ability thereof is increased, the triplet state energy level of the acceptor units is reduced, and the property of the intramolecular charge transfer state is enhanced, so that the light-emitting molecules are redshifted, thereby realizing the preparation of the thermally activated delayed fluorescent material with a high efficiency of deep-red emission. In addition, by adjusting the number of the donor units and the binding positions thereof with the acceptor units, the interaction between the light-emitting molecules is reduced, thereby enhancing the luminous efficiency of the light-emitting molecules. The organic electroluminescent devices based on the thermally activated delayed fluorescent material with deep-red emission synthesized by the present application have the high external quantum efficiency and the slow decay efficiency.

BRIEF DESCRIPTION OF THE SEVERAL VIEWS OF THE DRAWINGS

In order to more clearly illustrate the technical solutions in the embodiments or the prior art, the following drawings, which are intended to be used in the description of the embodiments or the prior art, will be briefly described. It is obvious that the drawings and the following description are only some embodiments of the present disclosure. Those of ordinary skill in the art may, without creative efforts, can derive other drawings from these drawings.

DETAILED DESCRIPTION OF SPECIFIC EMBODIMENTS OF THE INVENTION

Figure 1:
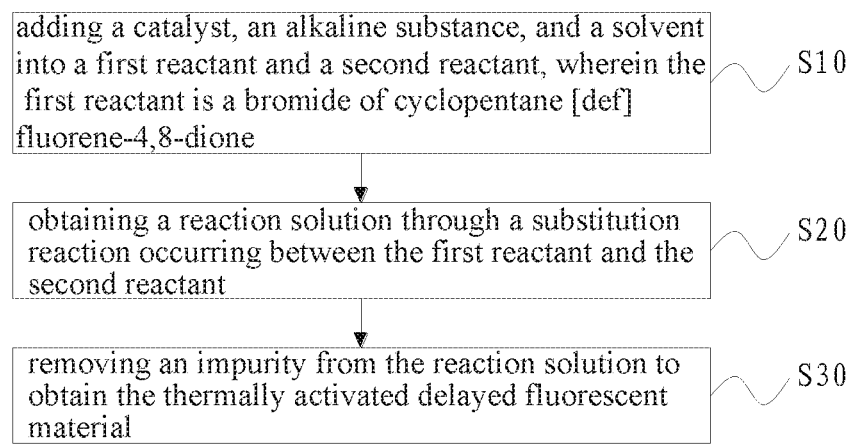
FIG. 1 is a schematic flowchart of a method of preparing thermally activated delayed fluorescent material according to an embodiment of the present application.

The following clearly and completely describes the technical solutions in the embodiments of the present application with reference to the accompanying drawings in the embodiments of the present application. Apparently, the described embodiments are merely some but not all of the embodiments of the present application. All other embodiments obtained by a person skilled in the art based on the embodiments of the present application without creative efforts shall fall within the protection scope of the present application.

In the description of the present application, it is to be understood that terms "center", "longitudinal", "transverse", "length", "width", "thickness", "upper", "lower, "front", "rear", "left", "right", "vertical", "horizontal", "top", "bottom", "inner", "outer", "clockwise", "counterclockwise and the like indicate orientations and position relationships which are based on the illustrations in the accompanying drawings, and these terms are merely for ease and brevity of the description, instead of indicating or implying that the devices or elements shall have a particular orientation and shall be structured and operated based on the particular orientation. Accordingly, these terms shall not be construed as limiting the present application. Moreover, terms such as "first" and "second" are used herein for purposes of description and are not intended to indicate or imply relative importance or significance or to imply the number of indicated technical features. Therefore, the features defined by the terms "first" and "second" may explicitly or implicitly include one or more of these features. In addition, in the description of the present application, "a plurality of" means two or more than two, unless specified otherwise.

It should be noted that in the description of the present application, unless expressly stated and defined otherwise, terms "mounting", "mutually connect", and "connection" should be interpreted broadly. For example, it may be a fixed connection, a detachable connection or an integral connection; it may be a mechanical connection, an electrical connection, or a mutual communication; it may be a direct connection, an indirect connection via an intermediate medium, or an internal communication between two elements. For those skilled in the art, specific meanings of the above terms in the present application may be interpreted in accordance with specific conditions.

In the present application, unless explicitly specified and defined otherwise, a first feature being "above" or "below" a second feature may include the first feature and the second feature being in direct contact, and may also include the first feature and the second feature being in non-direct contact via another feature therebetween. Further, the first feature being "over", "above" or "on the top of" the second feature includes the first feature being directly above and obliquely above the second feature, or merely indicates the horizontal height of the first feature being higher than that of the second feature. The first feature being "under", "below" or "underneath" the second feature includes the first feature being directly below and obliquely below the second feature, or merely indicates that the horizontal height of the first feature is lower than that of the second feature.

The following application provides a plurality of different embodiments or examples to implement different structures of the present application. To simplify the application of the present application, the following describes components and settings in particular examples. Certainly, the examples are merely for illustrative purposes, and are not intended to limit the present application. In addition, in the present application, reference numerals and/or reference letters may be repeated in different examples. This repetition is for the purpose of simplicity and clarity, and does not indicate a relationship between the various embodiments and/or settings that are discussed. In addition, the present application provides examples of various particular processes and materials, but a person of ordinary skill in the art will recognize that other processes and/or materials may be applied and/or used.

An embodiment of the present application provides a thermally activated delayed fluorescent material, having a structural formula shown in the following formula I:

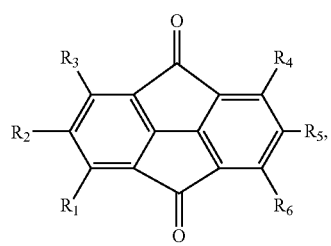

I wherein $R_1$-$R_6$ are electron donor units. The molecular formula of the thermally activated delayed fluorescent material in the example of the present application uses cyclopenta[def]fluorene-4,8-dione as electron acceptor units to combine with different $R_1$-$R_6$ electron donor units, thereby constructing a series of D-A-D type light-emitting molecules. By adjusting the types of $R_1$-$R_6$ (i.e., adjusting the positions and number of the electron donor units connected to the electron acceptor units), the interaction between the light-emitting molecules is reduced, thereby improving the luminous efficiency of the light-emitting molecules. By adding a carbonyl group in a ring to the fluorenone of the electron acceptor unit in the embodiment, the conjugated effect of the acceptor units of the light-emitting molecules is increased, the electron withdrawing ability thereof is increased, the triplet state energy level of the electron acceptor units is reduced, and the property of the intramolecular charge transfer state is enhanced, so that the light-emitting molecules are redshifted, thereby realizing the preparation of the thermally activated delayed fluorescent material (TADF) with a high efficiency of deep-red emission.

For example, $R_1$-$R_6$ may be selected from one of the following structural formulas, but is not limited to the following structural formulas:

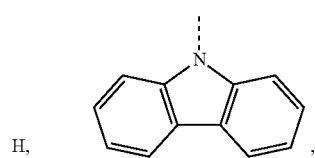

H,

-continued

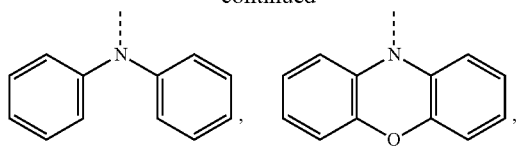

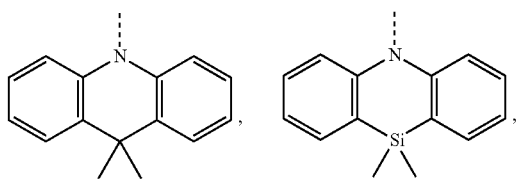

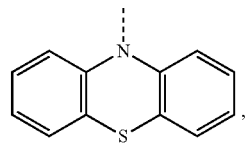

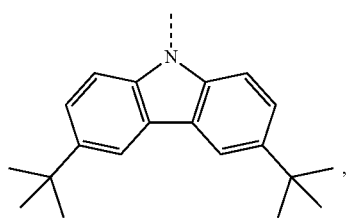

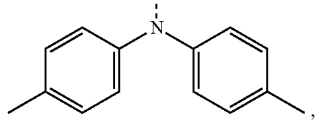

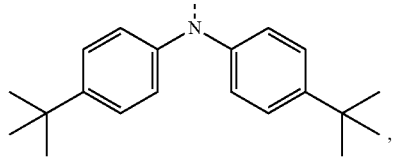

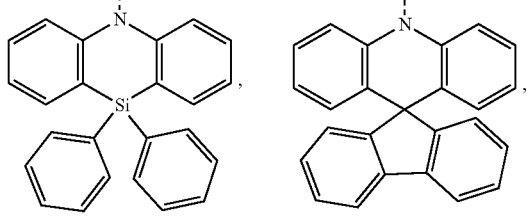

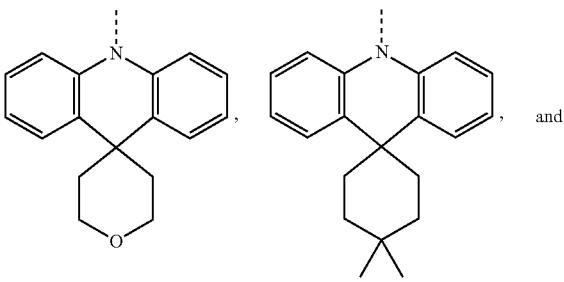

, and

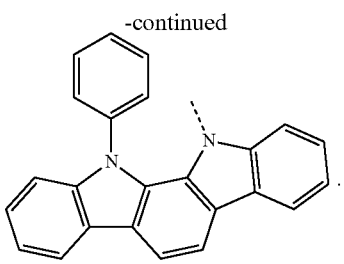

$R_1$-$R_6$ may be the same or different. The thermally activated delayed fluorescent material may be used in organic electroluminescent devices as luminescent guest material, or directly used as luminescent material. The organic electroluminescent devices based on the above-mentioned thermally activated delayed fluorescent material have the high external quantum efficiency and the low decay efficiency.

As shown in FIG. 1, based on the above purpose, an embodiment of the present application further provides a method of preparing the above thermally activated delayed fluorescent material, including the following steps:

a step S10 of adding a catalyst, an alkaline substance, and a solvent into a first reactant and a second reactant, wherein the first reactant is a bromide of cyclopenta[def]fluorene-4,8-dione;

a step S20 of obtaining a reaction solution through a substitution reaction occurring between the first reactant and the second reactant; and a step S30 of removing an impurity from the reaction solution to obtain the thermally activated delayed fluorescent material having a structural formula of:

I

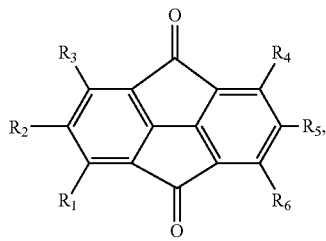

wherein $R_1$-$R_6$ are electron donor units.

The second reactant may be one or any combination of a hydride of $R_1$, a hydride of $R_2$, a hydride of $R_3$, a hydride of $R_4$, a hydride of $R_5$, and a hydride of $R_6$.

The catalyst may be palladium catalyst, the alkaline substance may be sodium tert-butoxide (NaOt-Bu), and the solvent may be anhydrous toluene. Specifically, the catalyst may be tris(dibenzylideneacetone)dipalladium(0) ($Pd_2(dba)_3$). In addition, a catalyst ligand may be added to the substitution reaction, for example, (OXYDI-2,1-PHENYLENE)BIS(DIPHENYLPHOSPHINE).

In the substitution reaction, the added amount of the second reactant may be slightly excessive relative to the added amount of the first reactant, so that the substitution reaction proceeds in a direction where the conversion rate of the first reactant is high. For example, the ratio of the molar mass of the second reactant to the molar mass of bromine atoms in the first reactant may be 1.05-1.1:1.

The temperature of the substitution reaction may be 80 degrees Celsius, and the reaction time may be 24 hours.

The reaction solution obtained by the substitution reaction can be purified by column chromatography, specifically including: pouring the reaction solution into saturated saline, and conducting suction filtration to obtain a red solid; and isolating and purifying the red solid by column chromatography to obtain the thermally activated delayed fluorescent material.

The first reactant may be one of monobromide, dibromide, tribromide, and tetrabromide of cyclopenta[def]fluorene-4,8-dione. The first reactant can be synthesized by a substitution reaction occurring between cyclopenta[def]fluorene-4,8-dione and bromine. For example, the following synthetic route may be adopted to synthesize the above first reactant:

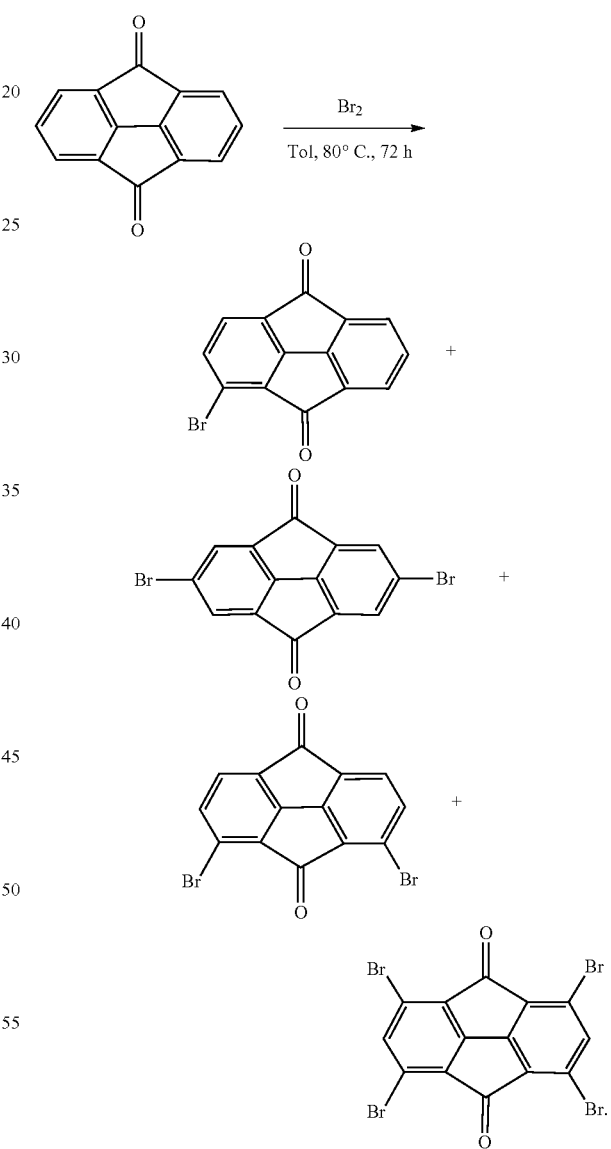

Cyclopenta[def]fluorene-4,8-dione (6.18 g, 30 mmol) is added to a 250 mL single-necked bottle filled with 80 mL, and 6 mL of bromine is pumped into the 250 ml single-necked bottle to react at 80° C. for 72 hours so as to obtain a reaction solution. After the reaction solution is cooled to room temperature, 100 ml of saturated sodium thiosulfate solution is slowly poured into the reaction solution, and suction filtration is conducted to obtain a yellow solid mixture. The yellow solid mixture is separated and purified by column chromatography (eluent: dichloromethane) to obtain bromides of cyclopenta[def]fluorene-4,8-dione: 1-bromocyclopenta[def]fluorene-4,8-dione (0.51 g, yield: 6%, MS (EI) m/z: [M]$^+$ calcd for $C_{14}H_5BrO_2$, 283.95; found, 283.99); 2,6-dibromocyclopenta[def]fluorene-4,8-dione (0.98 g, yield: 9%, MS (EI) m/z: [M]$^+$ calcd for $C_{14}H_4Br_2O_2$, 363.86; found, 363.83); 1,7-dibromocyclopenta[def]fluorene-4,8-dione (1.12 g, yield: 11%, MS(EI) m/z: [M]$^+$ calcd for $C_{14}H_4Br_2O_2$, 363.86; found, 363.88); 1,3,5,7-tetrabromocyclopenta[def]fluorene-4,8-dione (1.10 g, yield: 7%, MS (EI) m/z: [M]$^+$ calcd for $C_{14}H_2Br_4O_2$, 521.67; found, 521.69).

The thermal activation delayed fluorescent material of the present application and the method of preparing the same will be described in detail below with reference to specific examples.

Example 1

The first reactant in this example is 2,6-dibromocyclopenta[def]fluorene-4,8-dione, the second reactant is 9,10-dihydro-9,9-dimethylacridine, the catalyst is tris (dibenzylideneacetone) dipalladium, and the catalyst ligand is bis (2-diphenylphosphorphenyl) ether. The molar ratio of the first reactant to the second reactant is 1:2.1. A substitution reaction occurs between the first reactant and the second reactant to synthesize a target compound 1, having a structural formula of

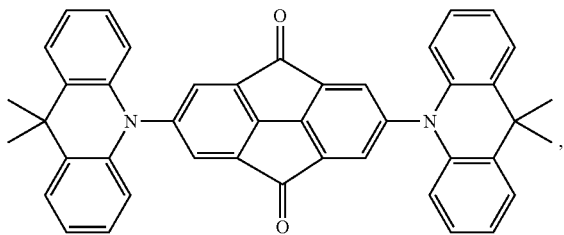

and a synthetic route of the target compound 1 is as follows:

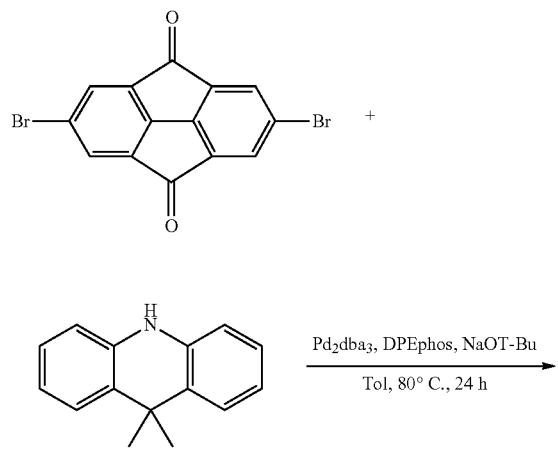

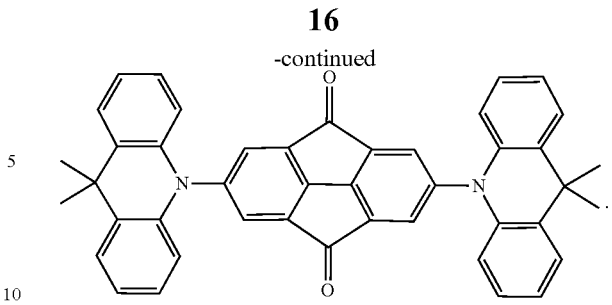

Specifically, 2,6-dibromocyclopenta[def]fluorene-4,8-dione (3.64 g, 10 mmol), 9,10-dihydro-9,9-dimethylacridine (4.40 g, 21 mmol), tris (dibenzylideneacetone) dipalladium (92 mg, 0.1 mmol), bis (2-diphenylphosphorphenyl) ether (108 mg, 0.2 mmol), and sodium tert-butoxide (2.0 g, 21 mmol) are added to a 250 mL single-necked bottle to pump three times, and then 80 mL of anhydrous toluene is pumped into the single-necked bottle under argon atmosphere to react at 80° C. for 24 hours so as to obtain a reaction solution. After the reaction solution is cooled to room temperature, the reaction solution is poured into 200 mL of saturated saline, and suction filtration is conducted to obtain a red solid product. The red solid product is separated and purified by column chromatography (eluent: methylene chloride:n-hexane, v:v, 1:1) to obtain a red powder compound 1 (4.66 g, yield: 75%). MS (EI) m/z: [M]$^+$ calcd for $C_{44}H_{32}N_2O_2$, 620.25; found, 620.38.

Figure 2:
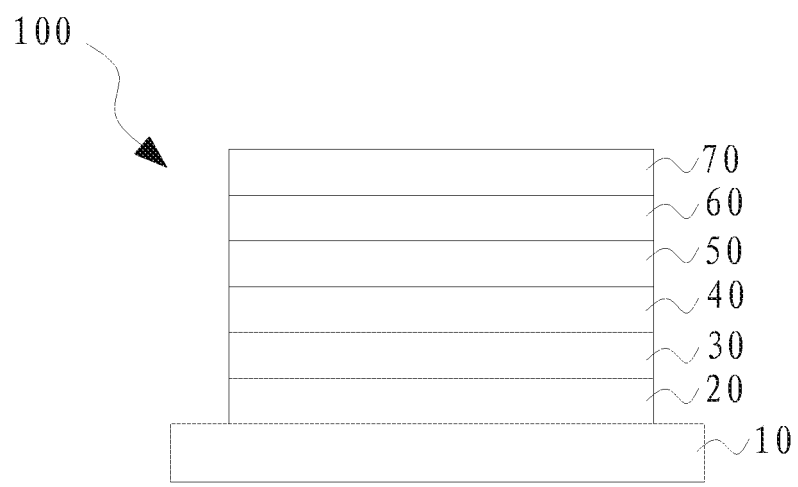
FIG. 2 is a schematic structural diagram of an organic electroluminescent device according to an embodiment of the present application.

As shown in FIG. 2, this example further provides an organic electroluminescent device 100 including an anode layer 20, a cathode layer 70, and a light emitting layer disposed between the anode layer 20 and the cathode layer 70. The light-emitting layer includes the thermally activated delayed fluorescent material prepared by the above method, i.e., the target compound 1.

The light-emitting layer includes a hole transport layer 30, an auxiliary layer 40, a luminescent material layer 50, and an electron transport layer 60 provided sequentially.

The organic electroluminescent device 100 further includes a substrate 10, which may include a glass substrate, and may further include a thin film transistor array disposed on the glass substrate.

The anode layer 20 is disposed on the substrate 10, and material of the anode layer 20 may be indium tin oxide.

Material of the hole transport layer 30 may be 4,4'-cyclohexylbis[N, N-bis (4-methylphenyl) aniline] (TAPC), and a thickness of the hole transport layer 30 may be 30 nanometers (nm).

Material of the auxiliary layer 40 may be 4,4', 4"-tris (carbazol-9-yl) triphenylamine (TCTA), and a thickness of the auxiliary layer 40 may be 5 nm.

The luminescent material layer 50 can be manufactured by co-doping the host luminescent material and the guest luminescent material. The target compound 1 synthesized in this example is used as the guest luminescent material in the luminescent material layer 50. The mass percentage of the target compound 1 in the luminescent material layer 50 is 1%. A thickness of the luminescent material layer 50 may be 15 nm.

Material of the electron transport layer 60 may be 1,3,5-tris (3-(3-pyridyl) phenyl) benzene (TmPyPB), and a thickness of the electron transport layer 60 may be 65 nm.

Material of the cathode layer may be an alloy of lithium fluoride and aluminum, a thickness of the lithium fluoride of a bottom layer may be 1 nm, and a thickness of the aluminum of a top layer may be 100 nm.

The manufacture of the organic electroluminescent device 100 includes steps of: under high vacuum, sequentially vapor-depositing the hole transport layer 30, the auxiliary layer 40, the luminescent material layer 50, the electron transport layer 60, the lithium fluoride film layer, and the aluminum film layer on the cleaned substrate 10 formed with the anode layer 20.

Example 2

The synthesis method of a target compound 2 provided in this example is the same as that in example 1, except that the first reactant is 1,7-dibromocyclopenta[def]fluorene-4,8-dione. The structural formula of the target compound 2 is:

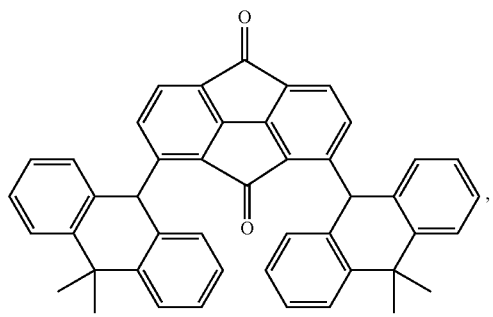 [SMILES: CC1(C)c2ccccc2C(c2ccc3c4c2c(=O)c2c(C5c6ccccc6C(C)(C)c6ccccc65)ccc(c2-4)c3=O)c2ccccc21]

and a synthetic route of the target compound 2 is as follows:

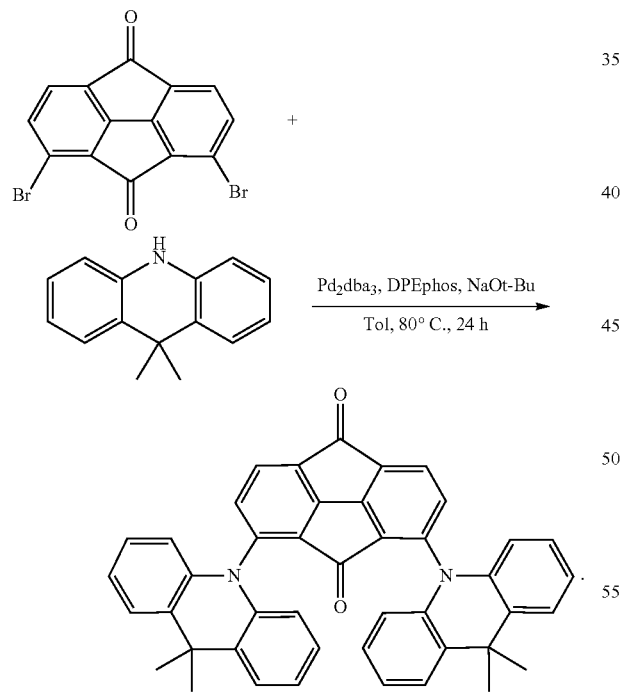

Specifically, 1,7-dibromocyclopenta[def]fluorene-4,8-dione (3.64 g, 10 mmol), 9,10-dihydro-9,9-dimethylacridine (4.40 g, 21 mmol), tris (dibenzylideneacetone) dipalladium (92 mg, 0.1 mmol), bis (2-diphenylphosphorphenyl) ether (108 mg, 0.2 mmol), and sodium tert-butoxide (2.0 g, 21 mmol) are added to a 250 mL single-necked bottle to pump three times, and then 80 mL of anhydrous toluene is pumped into the single-necked bottle under argon atmosphere to react at 80° C. for 24 hours so as to obtain a reaction solution. After the reaction solution is cooled to room temperature, the reaction solution is poured into 200 mL of saturated saline, and suction filtration is conducted to obtain a red solid product. The red solid product is separated and purified by column chromatography (eluent: methylene chloride:n-hexane, v:v, 1:1) to obtain a red powder compound 1 (4.53 g, yield: 73%). MS (EI) m/z: $[M]^+$ calcd for $C_{44}H_{32}N_2O_2$, 620.25; found, 620.33.

The guest luminescent material of the luminescent material layer of the organic electroluminescent device provided in this example is the target compound 2. The other structures are the same as those in the first example mentioned above, and will not be repeated here.

Example 3

The first reactant in this example is 1-bromocyclopenta[def]fluorene-4,8-dione, and the second reactant is 9,10-dihydro-9,9-dimethylacridine. The structural formula of the target compound 3 provided in this example is:

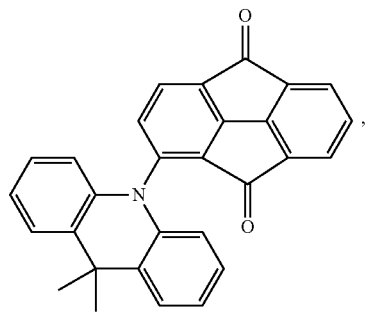 [SMILES: CC1(C)c2ccccc2N(c2ccc3c4c2c(=O)c2cccc(c2-4)c3=O)c2ccccc21]

and a synthetic route of the target compound 3 is as follows:

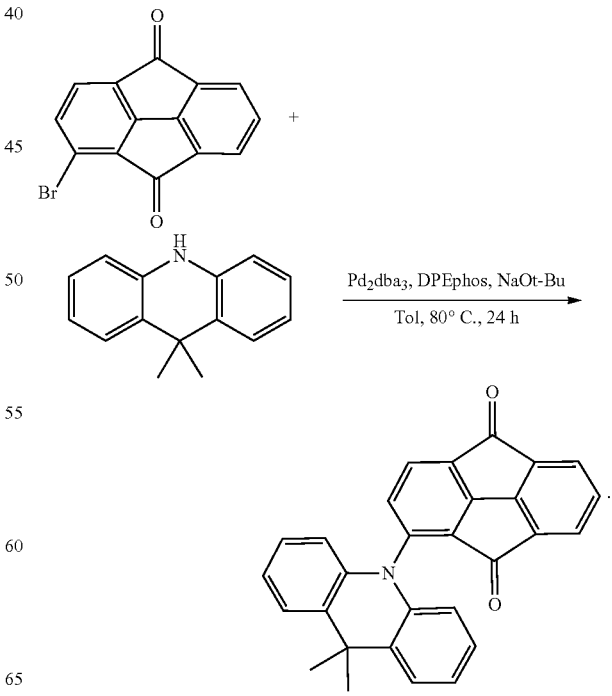

Specifically, 1-bromocyclopenta[def]fluorene-4,8-dione (2.85 g, 10 mmol), 9,10-dihydro-9,9-dimethylacridine (2.20 g, 10.5 mmol), tris (dibenzylideneacetone) dipalladium (92 mg, 0.1 mmol), bis (2-diphenylphosphorphenyl) ether (108 mg, 0.2 mmol), and sodium tert-butoxide (1.0 g, 10.5 mmol) are added to a 150 mL single-necked bottle to pump three times, and then 60 mL of anhydrous toluene is pumped into the single-necked bottle under argon atmosphere to react at 80° C. for 24 hours so as to obtain a reaction solution. After the reaction solution is cooled to room temperature, the reaction solution is poured into 200 mL of saturated saline, and suction filtration is conducted to obtain a red solid product. The red solid product is separated and purified by column chromatography (eluent: methylene chloride:n-hexane, v:v, 1:1) to obtain a red powder compound 3 (3.35 g, yield: 81%). MS (EI) m/z: [M]$^+$ calcd for $C_{29}H_{19}NO_2$, 413.14; found, 413.39.

The guest luminescent material of the luminescent material layer of the organic electroluminescent device provided in this example is the target compound 3. The other structures are the same as those in the above examples, and will not be repeated here.

Example 4

The first reactant in this example is 1,3,5,7-tetrabromo-cyclopenta[def]fluorene-4,8-dione, and the second reactant is 9,10-dihydro-9,9-dimethylacridine. The structural formula of the target compound 4 provided in this example is;

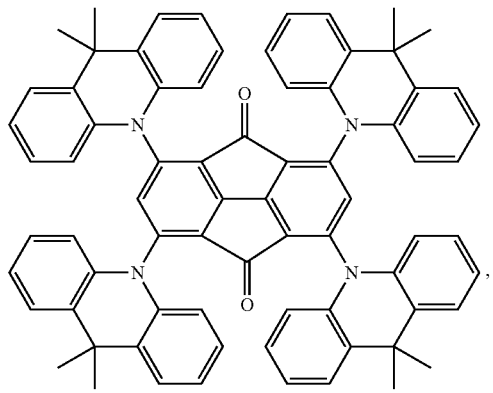 [SMILES: CC1(C)c2ccccc2N(c2cc(N3c4ccccc4C(C)(C)c4ccccc43)c3c4c2c(=O)c2c(N5c6ccccc6C(C)(C)c6ccccc65)cc(N5c6ccccc6C(C)(C)c6ccccc65)c(c2-4)c3=O)c2ccccc21]

and a synthetic route of the target compound 4 is as follows:

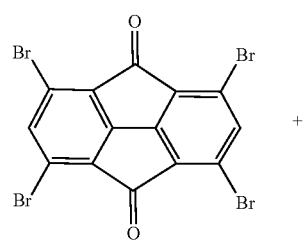

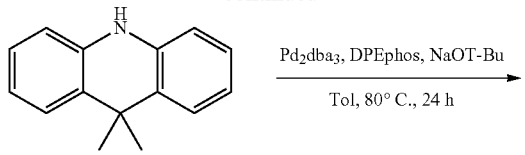

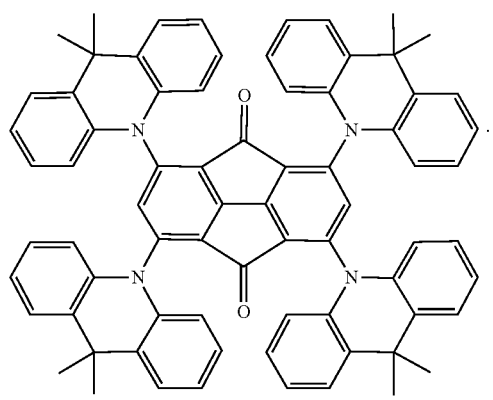

Specifically, 1,3,5,7-tetrabromocyclopenta[def]fluorene-4,8-dione (5.22 g, 10 mmol), 9,10-dihydro-9,9-dimethylacridine (8.80 g, 42 mmol), tris (dibenzylideneacetone) dipalladium (92 mg, 0.1 mmol), bis (2-diphenylphosphorphenyl) ether (108 mg, 0.2 mmol), and sodium tert-butoxide (4.03 g, 42 mmol) are added to a 250 mL single-necked bottle to pump three times, and then 100 mL of anhydrous toluene is pumped into the single-necked bottle under argon atmosphere to react at 80° C. for 24 hours, so as to obtain a reaction solution. After the reaction solution is cooled to room temperature, the reaction solution is poured into 200 mL of saturated saline, and suction filtration is conducted to obtain a red solid product. The red solid product is separated and purified by column chromatography (eluent: methylene chloride:n-hexane, v:v, 1:1) to obtain a red powder compound 4 (6.94 g, yield: 67%). MS (EI) m/z: [M]$^+$ calcd for $C_{74}H_{58}N_4O_2$, 1034.46; found, 1034.53.

The guest luminescent material of the luminescent material layer of the organic electroluminescent device provided in this example is the target compound 4. The other structures are the same as those in the above examples, and will not be repeated here.

Example 5

The first reactant in this example is 1,3,5,7-tetrabromo-cyclopenta[def]fluorene-4,8-dione, and the second reactant is 9,10-dihydro-9,9-dimethylacridine. The structural formula of the target compound 5 provided in this example is;

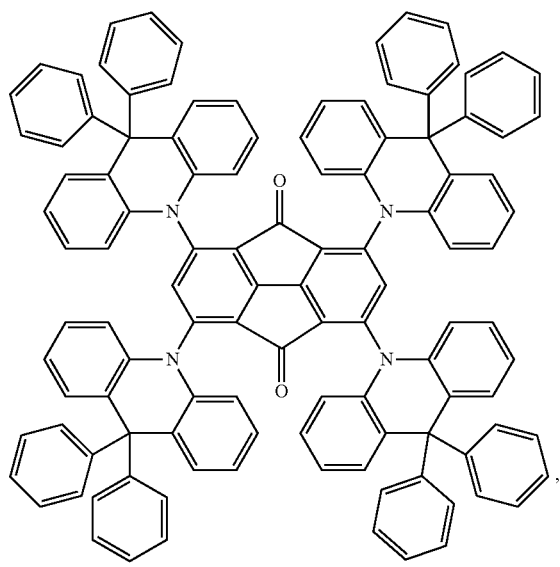 [SMILES: O=c1c2c(N3c4ccccc4C(c4ccccc4)(c4ccccc4)c4ccccc43)cc(N3c4ccccc4C(c4ccccc4)(c4ccccc4)c4ccccc43)c3c2-c2c1c(N1c4ccccc4C(c4ccccc4)(c4ccccc4)c4ccccc41)cc(N1c4ccccc4C(c4ccccc4)(c4ccccc4)c4ccccc41)c2c3=O]

and a synthetic route of the target compound 5 is as follows:

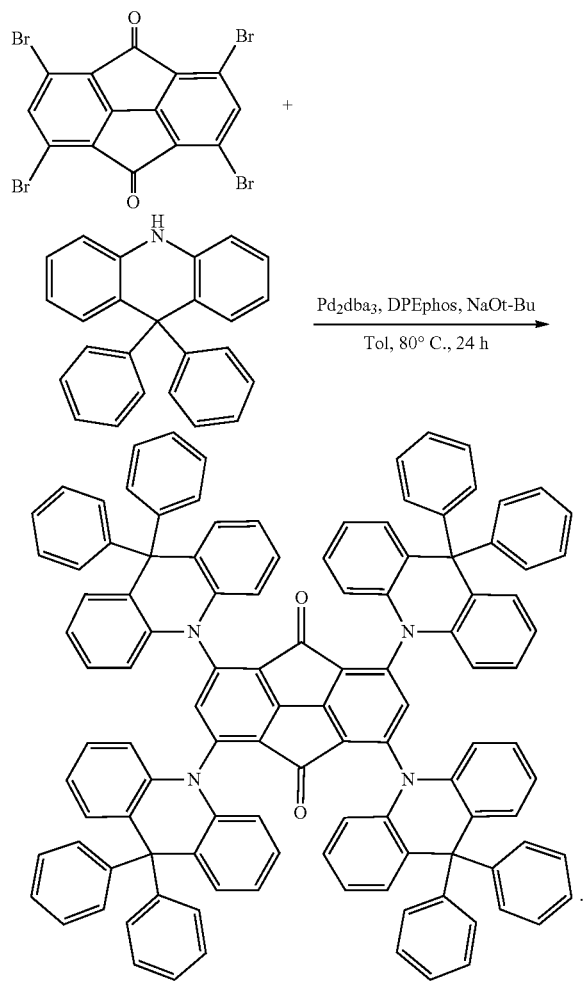

Specifically, 1,3,5,7-tetrabromocyclopenta[def]fluorene-4,8-dione (5.22 g, 10 mmol), 9,10-dihydro-9,9-dimethyl-acridine (14.0 g, 42 mmol), tris (dibenzylideneacetone) dipalladium (92 mg, 0.1 mmol), bis (2-diphenylphosphorphenyl) ether (108 mg, 0.2 mmol), and sodium tert-butoxide (4.0 g, 42 mmol) are added to a 250 mL single-necked bottle to pump three times, and then 100 mL of anhydrous toluene is pumped into the single-necked bottle under argon atmosphere to react at 80° C. for 24 hours so as to obtain a reaction solution. After the reaction solution is cooled to room temperature, the reaction solution is poured into 200 mL of saturated saline, and suction filtration is conducted to obtain a red solid product. The red solid product is separated and purified by column chromatography (eluent: methylene chloride:n-hexane, v:v, 1:1) to obtain a red powder compound 5 (9.65 g, yield: 63%). MS (EI) m/z: $[M]^+$ calcd for $C_{114}H_{74}N_4O_2$, 1531.83; found, 1531.95.

The guest luminescent material of the luminescent material layer 50 of the organic electroluminescent device provided in this example is the target compound 5. The other structures are the same as those in the above examples, and will not be repeated here.

The target compounds in the five examples are respectively applied to organic electroluminescent devices, and the performance of each organic electroluminescent device is tested in the room temperature atmosphere. The highest brightness, the highest current efficiency, the CIE chromaticity coordinate, and the maximum external quantum efficiency of each organic electroluminescent device are shown in table 1 below, where D1-D5 correspond to the organic electroluminescent devices corresponding to the target compound 1 to the target compound 5, respectively.

TABLE 1

| Devices | Maximum brightness (cd/m²) | Maximum current efficiency (cd/A) | CIEx | Maximum external quantum efficiency (%) |
| --- | --- | --- | --- | --- |
| D1 | 2743 | 26.7 | 0.564 | 16.6 |
| D2 | 2695 | 25.5 | 0.569 | 15.7 |
| D3 | 2351 | 21.4 | 0.558 | 14.3 |
| D4 | 2142 | 19.6 | 0.574 | 13.5 |
| D5 | 2215 | 18.9 | 0.571 | 12.1 |

Beneficial Effect

By using the cyclopenta[def]fluorene-4,8-dione as the acceptor units, the conjugated effect of the molecular acceptor units is increased, the electron withdrawing ability thereof is increased, the triplet state energy level of the acceptor units is reduced, and the property of the intramolecular charge transfer state is enhanced, so that the light-emitting molecules are redshifted, thereby realizing the preparation of the thermally activated delayed fluorescent material with a high efficiency of deep-red emission. In addition, by adjusting the number of the donor units and the binding positions with the acceptor units, the interaction between the light-emitting molecules is reduced, thereby enhancing the luminous efficiency of the light-emitting molecules. The organic electroluminescent device based on the thermally activated delayed fluorescent material with deep-red emission synthesized by the present application has a high external quantum efficiency and a slow decay efficiency.

Each of the embodiments described above contains different emphasis. For contents which are not described in detail in a certain embodiment, reference may be made to the related description in the other embodiment.

A thermally activated delayed fluorescent material, preparing method thereof, and an organic electroluminescent device provided by the embodiments of the present application have been described in detail above. The present text uses specific examples for illustrating the principles and implementations of the present disclosure. The description of the above embodiments is merely used for facilitating the understanding of the methods and the core ideas of the present disclosure. It should be understood by those ordinary skilled in the art that various modifications and equivalent replacements of a part of technical features of the technical solutions of above-mentioned embodiments can be made, and these modifications and replacements should be deemed as within the protect scope of the disclosure.

What is claimed is:

1. An organic electroluminescent device, comprising: an anode layer, a cathode layer, and a light-emitting layer disposed between the anode layer and the cathode layer, wherein the light-emitting layer comprises a thermally activated delayed fluorescent material, and a structural formula of the thermally activated delayed fluorescent material is shown in the following structural formula I:

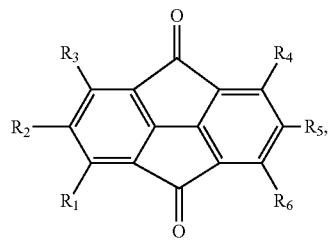

wherein $R_1$-$R_6$ are electron donor units.

2. The organic electroluminescent device of claim 1, wherein $R_1$-$R_6$ are independently selected from one of the following structural formulas:

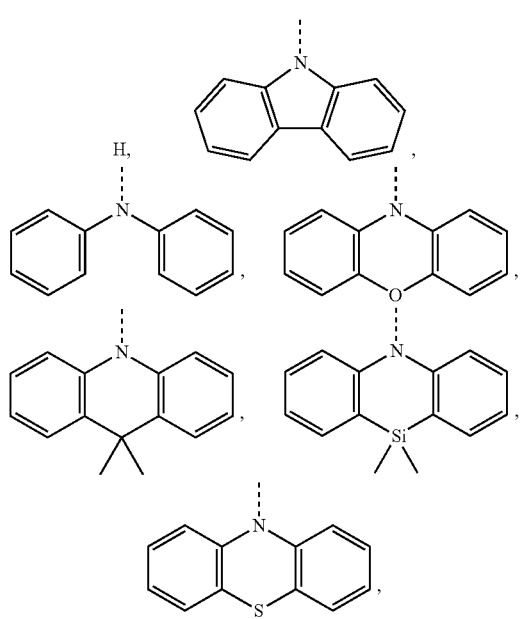

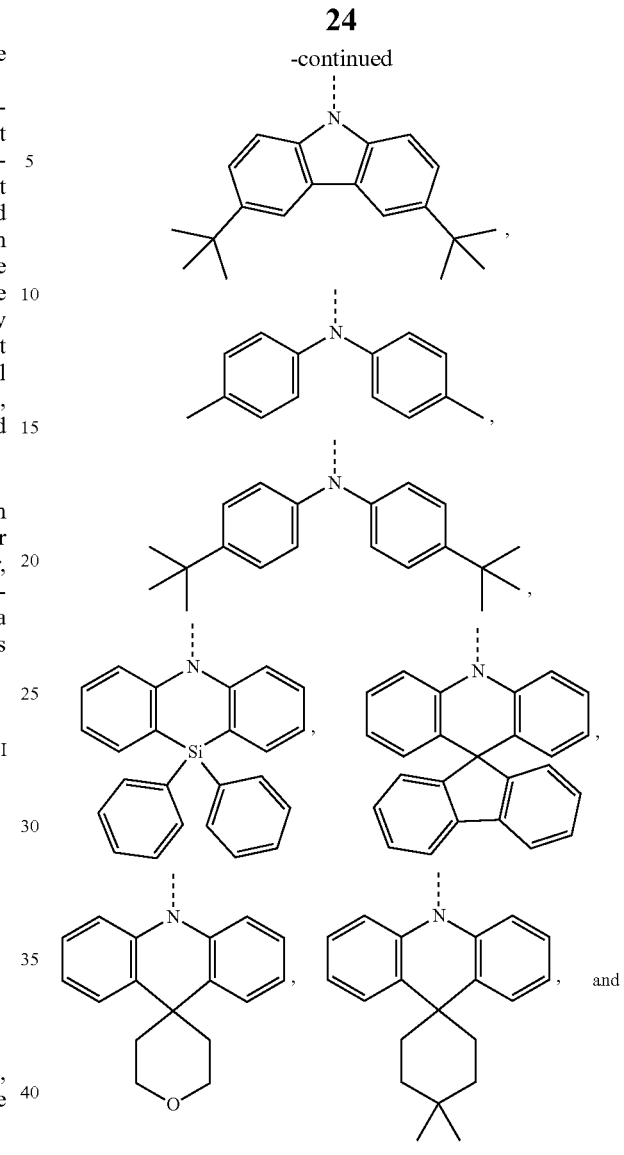

3. The organic electroluminescent device of claim 1, wherein a method of preparing the thermally activated delayed fluorescent material comprises:

a step S10 of adding a catalyst, an alkaline substance, and a solvent into a first reactant and a second reactant, wherein the first reactant is a bromide of cyclopenta [def]fluorene-4,8-dione;

a step S20 of obtaining a reaction solution through a substitution reaction occurring between the first reactant and the second reactant; and a step S30 of removing an impurity from the reaction solution to obtain the thermally activated delayed fluorescent material having the structural formula of:

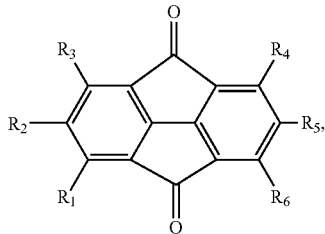

wherein $R_1$-$R_6$ are electron donor units.

4. The organic electroluminescent device of claim 3, wherein the second reactant is one or any combination of a hydride of $R_1$, a hydride of $R_2$, a hydride of $R_3$, a hydride of $R_4$, a hydride of $R_5$, and a hydride of $R_6$.

5. The organic electroluminescent device of claim 3, wherein the first reactant is selected from one of the following structural formulas:

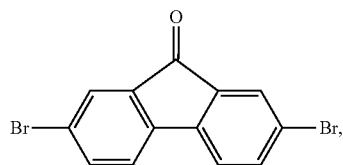

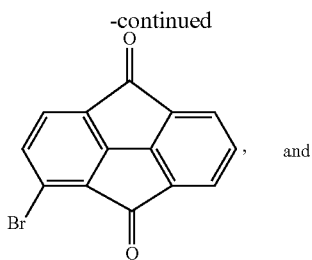

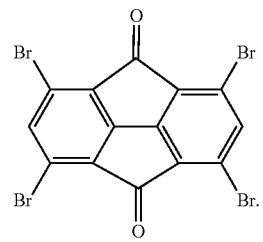

6. The organic electroluminescent device of claim 3, wherein the catalyst comprises tris (dibenzylideneacetone), the alkaline substance is sodium tert-butoxide, and the solvent is anhydrous toluene.

7. The organic electroluminescent device of claim 3, wherein a reaction temperature of the substitution reaction is 80 degrees Celsius, and a reaction time of the substitution reaction is 24 hours.

8. The organic electroluminescent device of claim 7, wherein the step S30 includes:
    pouring the reaction solution into saturated saline, and conducting suction filtration to obtain a red solid; and
    isolating and purifying the red solid by column chromatography to obtain the thermally activated delayed fluorescent material.

* * * * *